(12) United States Patent
Kaneko et al.

(10) Patent No.: US 11,684,072 B2
(45) Date of Patent: Jun. 27, 2023

(54) SOY MILK FERMENTED SUBSTANCE

(71) Applicant: KIKKOMAN CORPORATION, Noda (JP)

(72) Inventors: Daisuke Kaneko, Noda (JP); Kenji Aoyama, Noda (JP); Engels Wim, Ede (NL); Wegkamp Arno, Ede (NL); Kingma Fedde, Ede (NL)

(73) Assignee: KIKKOMAN CORPORATION, Noda (JP)

( * ) Notice: Subject to any disclaimer, the term of this patent is extended or adjusted under 35 U.S.C. 154(b) by 0 days.

(21) Appl. No.: 14/782,112

(22) PCT Filed: Apr. 2, 2014

(86) PCT No.: PCT/JP2014/059786
§ 371 (c)(1),
(2) Date: Oct. 2, 2015

(87) PCT Pub. No.: WO2014/163123
PCT Pub. Date: Oct. 9, 2014

(65) Prior Publication Data
US 2016/0044931 A1 Feb. 18, 2016

(30) Foreign Application Priority Data

Apr. 2, 2013 (JP) .............................. JP2013-076517

(51) Int. Cl.
| A23C 9/127 | (2006.01) |
| C12P 7/56 | (2006.01) |
| A23C 11/10 | (2021.01) |
| A23L 11/65 | (2021.01) |

(52) U.S. Cl.
CPC ............ *A23C 9/127* (2013.01); *A23C 11/106* (2013.01); *A23L 11/65* (2021.01); *C12P 7/56* (2013.01); *A23Y 2220/29* (2013.01); *A23Y 2240/75* (2013.01)

(58) Field of Classification Search
CPC ..... A23C 11/10; A23C 11/103; A23C 11/106; A23C 11/09; A13C 11/106; A23L 11/09; A23L 11/106
USPC ....................................................... 426/634
See application file for complete search history.

(56) References Cited

U.S. PATENT DOCUMENTS

2012/0177782 A1    7/2012 De Bok et al.

FOREIGN PATENT DOCUMENTS

| CN | 102948486 A | 3/2013 |
| EP | 0 386 817 A1 | 9/1990 |
| JP | 2002-176911 A | 6/2002 |
| JP | 2004-261003 A | 9/2004 |
| JP | 3748206 | 2/2006 |
| JP | 2011-167190 A | 9/2011 |

OTHER PUBLICATIONS

Farnworth et al., "Growth of probiotic bacteria and bifidobacteria in a soy yogurt formulation," International Journal of Food Microbiology, 116 (2007), 174-181 (Year: 2007).*
S. Chumchuere, et al., "Selection of starter cultures for the fermentation of soya milk", Food Microbiology, 1999, pp. 129-137, vol. 16, No. 2.
C.S. Favaro Trindade, et al., "Development and sensory evaluation of soy milk based yoghurt", Archives Latinoamericanos de Nutricion, 2001, pp. 100-104, vol. 51, No. 1.
Pei Hao, et al., "Complete Sequencing and Pan-Genomic Analysis of *Lactobacillus delbrueckii* subsp. *bulgaricus* Reveal its Genetic Basis for Industrial Yogurt Production", PLoS One, Jan. 2011, pp. 1-9, vol. 6, No. 1.
Jacques-Edouard Germond, et al., "Evolution of the Bacterial Species *Lactobacillus delbrueckii*: a Partial Genomic Study with Reflections on Prokaryotic Species Concept", Molecular Biology and Evolution, 2003, pp. 93-104, vol. 20, No. 1.
International Search Report for PCT/JP2014/059786 dated Jun. 24, 2014 [PCT/ISA/210].
Written Opinion for PCT/JP2014/059786 dated Jun. 24, 2014 [PCT/ISA/237].
Written Opinion dated Dec. 14, 2016, in counterpart Singaporean Application No. 11201508221X.
Written Opinion dated May 31, 2016, in counterpart Singaporean Application No. 11201508221X.
EP_F26174; Response filed May 9, 2017.
EPA Communication, EP_F26174, dated Oct. 25, 2016.
Lourens-Hattingh et al. (2001), "Yogurt as probiotic carrier food", International Dairy Journal, 11, 1-17. (p. 8 at the top right).
De Vos (1996), "Metabolic engineering of sugar catabolism in lactic acid bacteria", Antonie van Ieeuwenhoek, 70, 223-242. (p. 224 Table 1).
Mital et al. (1979), "Fermentation of soy milk by lactic acid bacteria. A Review", Journal of Food Protection, 42, 895-899. (p. 896 bottom right and p. 897 top right).
Rohm et al. (1990), "Microflora of Austrian natural-set yogurt", Journal of Food Protection, 53, 478-480. (p. 479 Figure 2).
Hamann et al. (1984), "Survival of *Streptococcus* thermophiles and Lactobacillus bulgaricus in commercial and experimental yogurt", Journal of Food Protection, 47, 781-786. (p. 783 Figure 1, Figure 2).
Medina et al. (1994), "Survival of constitutive microflora in commercially fermented milk containing Bifidobacteria during refrigerated storage", Journal of Food Protection, 56, 731-733. (p. 732 Table 1).

(Continued)

Primary Examiner — Jeffrey P Mornhinweg
(74) Attorney, Agent, or Firm — Sughrue Mion, PLLC

(57) ABSTRACT

A soy milk fermented substance is provided. The soy milk fermented substance has a taste and flavor or smooth physicality similar to that of yogurt obtained by fermenting milk with a lactic acid without applying processing treatment such as enzyme treatment or extraction treatment to soy milk which is a material and without adding a material such as a sugar source, even in a case where only *Streptococcus thermophilus* and *Lactobacillus delbrueckii* subsp. *bulgaricus* are employed as a lactic acid bacteria mixture starter at the time of making a fermented substance which employs soy milk as a material.

10 Claims, 12 Drawing Sheets

(56) References Cited

OTHER PUBLICATIONS

Taira et al. (1990), "Difference in sugar contents of soybeans cultured by upland and drained paddy field", Nippon Shokuhin Kogyo Gakkaishi, 37, 602-611. (p. 604 Table 2-1 and Table 2-2).
Hols et al. (2005), "New insights in the molecular biology and physiology of *Streptococcus* thermophiles revealed by comparative genomics", FEMS Microbiology Reviews, 29, 435-463. (p. 445 Fig. 3).
Sieuwerts et al. (2010), "Mixed-culture transcriptome analysis reveals the molecular basis of mixed-culture growth in *Streptococcus* thermophiles and lactobacillus bulgaricus" Applied and Environmental Microbiology, 76, 7775-7784. (p. 7782 bottom right).
Ngoc Tiet Le et al: "Fermented Soy Milk Using Lactic Acid Bacteria", mekongfood_1_proceedings, Jun. 11, 2012, pp. 33-36, XP055311435, Internet Retrieved from the Internet: URL:http://caab.ctu.edu.vn/dft/index.php?option=com_docman&task=doc_details&gid=5<emid=63 [retrieved on Oct. 17, 2016] the whole document, cited in ESR.
Sasaki et al. (1994). "Development of Gene Transfer Systems for Lactobacillus bulgaricus", Journal of the Brewering Society of Japan, 89, 613-619. (p. 615 at the bottom light).
Bergey's manual of systematic bacteriology second edition vol. 3 p. 484. (Table 84).
Bergey's manual of systematic bacteriology second edition vol. 3 p. 670. (Table 131).
Office Action dated Jan. 19, 2017 from Australian Government, IP Australia in AU Application No. 2014250456.
Response to Office Action dated Dec. 7, 2017 to Australian Government, IP Australia in AU Application No. 2014250456.
Office Action dated Nov. 1, 2018 from the State Intellectual Property Office of the P.R.C. in Application No. 201480020230.2.
Office Action dated May 12, 2020 from the State Intellectual Property Office of the P.R.C. in Application No. 201480020230.2.
Response to Office Action dated May 6, 2019 to the State Intellectual Property Office of the P.R.C. in Application No. 201480020230.2.
Response to Office Action dated Jul. 27, 2020 to the State Intellectual Property Office of the P.R.C. in Application No. 201480020230.2.
Extended European Search Report dated Oct. 25, 2016 from European Patent Office in EP Application No. 14779754.2.
Office Action dated Apr. 10, 2018 from European Patent Office in EP Application No. 14779754.2.
Office Action dated May 21, 2019 from European Patent Office in EP Application No. 14779754.2.
Response to Office Action dated May 9, 2017 to European Patent Office in EP Application No. 14779754.2.
Response to Office Action dated Oct. 5, 2018 to European Patent Office in EP Application No. 14779754.2.
Response to Office Action dated Nov. 29, 2019 to European Patent Office in EP Application No. 14779754.2.
Office Action dated Nov. 27, 2019 from the Intellectual Property India in Indian Application No. 9962/DELNP/2015.
Response to Office Action dated May 22, 2020 to the Intellectual Property India in Indian Application No. 9962/DELNP/2015.
Office Action dated Aug. 6, 2019 from Indonesian Patent Office in Indonesian Application No. P00201506945.
Response to Office Action dated Oct. 21, 2019 to Indonesian Patent Office in Indonesian Application No. P00201506945.
Office Action dated Jun. 26, 2020 from Korean Intellectual Property Office in Korean Application No. 10-2015-7026456.
Response to Office Action dated Aug. 24, 2020 to Korean Intellectual Property Office in Korean Application No. 10-2015-7026456.
Office Action dated Jun. 28, 2016 from the Intellectual Property Office of Singapore in Singaporean Application No. 11201508221X.
Office Action dated Jan. 9, 2017 from the Intellectual Property Office of Singapore in Singaporean Application No. 11201508221X.
Response to Office Action dated Nov. 28, 2016 to the Intellectual Property Office of Singapore in Singaporean Application No. 11201508221X.
Response to Office Action dated Jun. 7, 2017 to the Intellectual Property Office of Singapore in Singaporean Application No. 11201508221X.
Office Action dated Dec. 19, 2019 from the Vietnamese Intellectual Property Office in Vietnamese Application No. 1-2015-04104.
Response to Office Action dated Mar. 13, 2020 to the Vietnamese Intellectual Property Office in Vietnamese Application No. 1-2015-04104.
Wang et al., "Sugar and acid contents in soymilk fermented with lactic acid bacteria alone or simultaneously with bifidobacteria", Food Microbiology, Jun. 2003, vol. 20, Issue 3, pp. 333-338 (total 7 pages).
Ngoc Tiet et al., "Fermented Soy Mil using lactic acid bacteria", mekongfood_1_proceedings, Jun. 11, 2012, Xp055311435, pp. 33-36 (total 4 pages).
Wang et al., "Sugar and acid contents in soymilk fermented with lactic acid bacteria alone or simultaneously with bifidobacteria", Food Microbiology, 2003, vol. 20, XP0555463162, pp. 333-338 (total 6 pages).

* cited by examiner

SOY MILK FERMENTED SUBSTANCE

TECHNICAL FIELD

The present invention relates to a soy milk fermented substance obtained by fermenting soy milk with lactic acid bacteria.

BACKGROUND ART

Soybean is referred to as "a meat of the field", and is a food material including a rich vegetable protein, and soy milk is a milky drink obtained by eluting a protein. Soy milk can be fermented by lactic acid bacteria having a healthy function on its host, and the resulting product is very similar to yogurt. Because both soymilk and lactic acid bacteria are healthy materials, the soy milk fermented product is anticipated to have the synergetic healthy function. However, unpleasant odor peculiar to soybean or fermentation odor or pickles like odor generated by lactic acid bacteria has been an obstacle to the creation of the market of the fermented soy milk products.

On the other hand, in milk, it has been conventionally known that Streptococcus thermophilus and Lactobacillus delbrueckii sub sp. bulgaricus, which are defined as lactic acid bacteria for yogurt by CODEX determined by the Joint FAO/WHO Food Standard Committee (CODEX Alimentarius) (hereinafter, referred to as "CODEX"), establish a symbiotic relationship. It is also known that, by establishing this symbiotic relationship, growth of both bacterial species is remarkably improved in comparison with single strain fermentation, resulting in yogurt with a good taste and flavor.

However, in soy milk, even if Streptococcus thermophilus and Lactobacillus delbrueckii subsp. bulgaricus are inoculated simultaneously, fermentation does not proceed sufficiently, without adding lactose to soy milk and it is known to be difficult to form a card with a good physicality and to generate a good taste and flavor by production of lactic acid. The main cause of this difficulty is that Lactobacillus delbrueckii subsp. bulgaricus is not capable of assimilating sucrose contained in soy milk, and it is impossible to carry out lactic acid fermentation normally and increase the number of bacteria.

Up to now, there have been a number of methods of making a soy milk fermented substance with a good taste and flavor by lactic acid fermentation. For example, there is a method for improving a taste and flavor by mixing culture of five types of lactic acid bacteria, Lactobacillus acidophilus, Lactobacillus casei, Lactobacillus delbrueckii subsp. bulgaricus, Lactococus lactis, and Streptococcus thermophilus, and adding sugar, lipid, gelatin to un-modified pure soy milk (refer to Patent Literature 1).

Also, there has been a variety of reports of promoting lactic acid fermentation in soy milk and improving a taste and flavor by adding further different bacterial species to Streptcocus thermophilus and Lactobacillus debrueckii subsp. bulgaricus, or substituting these bacterial species completely by other bacterial species, such as; a method for improving a taste and flavor by fermenting two types of lactic acid bacteria, Lactobacillus plantarum and Lactococus lactis (refer to Patent Literature 2); a method for obtaining a soy milk fermented substance with an improved flavor by fermentation with at least three bacterial species, either Lactobacillus acidophilus or Lactobacillus casei, Bifidobacterium species, and Lactobacillus debrueckii subsp. bulgaricus (refer to Patent Literature 3); and a method for fermenting soy milk with three types of lactic acid bacteria; one bacterial strain selected from Lactobacillus debrueckii subsp. bulgaricus and Lactobacillus acidophilus; Lactobacillus casei; and Streptococcus thermophilus (refer to Patent Literature 4). In addition, there has been reported a method for carrying out fermentation by simultaneously adding sugar and a lactic acid bacteria and protease in soy milk in order to improve a taste and flavor (refer to Patent Literature 5).

CITATION LIST

Patent Literature

Patent Literature 1; Japanese Unexamined Patent Application Publication No. 63-7743
Patent Literature 2; Japanese Unexamined Patent Application Publication No. 5-184320
Patent Literature 3: Japanese Unexamined Patent Application Publication No. 10-201415
Patent Literature 4: Japanese Unexamined Patent Application Publication No. 2011-167190
Patent Literature 5: Japanese Unexamined Patent Application Publication No. 7-147898

SUMMARY OF THE INVENTION

Problems to be Solved by the Invention

However, in these prior arts, soy milk is fermented by using not only two lactic acid bacteria, Streptococcus thermophilus and Lactobacillus debrueckii subsp. bulgaricus, which are lactic acid bacteria for yogurt defined by CODEX, but also other species of lactic acid bacteria which have different properties from these two lactic acid bacteria; and therefore, there has been a problem that rough taste or pickles odor results from such different lactic acid bacteria and the fermented soy milk has significantly different flavor and physicality from those of yogurt obtained by fermenting cow milk. In addition, there are other problems that cumbersome work results from treating three or more strains of lactic acid bacteria in fermentation process, making it difficult to maintain the quality of production lots, and that cumbersome work results from formulating some food materials other than a soybean-derived material or adding enzymes to soy milk simultaneously to lactic acid inoculation.

Therefore, it is a problem to be solved by the present invention to provide a soy milk fermented substance with a taste and flavor or smooth physicality similar to that of yogurt obtained by fermenting cow milk with a lactic acid bacteria without applying processing treatment such as enzyme treatment or extraction treatment to soy milk which is a material, and also without adding a material such as a sugar source to the soy milk, even in a case where only Streptococcus thermophilus and Lactobacillus delbrueckii subsp. bulgaricus are employed as a lactic acid bacteria mixture starter at the time of making a fermented product which employs only soy milk as a material.

Means for Solving the Problem

As a result of carrying out utmost study in order to solve the problems described above, the Inventor, et al., found out that, in a lactic acid bacteria mixture starter obtained by combining two lactic acid bacteria, Streptococcus thermophilus and Lactobacillus debrueckii subsp. bulgaricus which are lactic acid bacteria for yogurt defined by CODEX, with each other, *Streptococcus thermophilus* which is capable of accumulating 0.4 g/L of fructose in soy milk and *Lactobacillus debrueckii* subsp. *bulgaricus* which is capable of generating 0.4 g/L or more of D-lactic acid when combined with the same *Streptococcus thermophilus* are combined with each other, whereby, in the soy milk environment as well, both two species of bacteria are grown to an extent such that the growth is substantially identical to that in the cow milk environment, and the soy milk fermented substance having taste and flavor or physicality similar to that of yogurt obtained by fermenting cow milk with a lactic acid bacteria is obtained, and achieved the present invention.

That is, the present invention provides (1) a soy milk fermented substance obtained by using a lactic acid bacteria mixture starter including: *Streptococcus thermophilus* which is capable of accumulating 0.4 g/L or more of fructose in the fermented substance when soy milk is inoculated with the strain and cultured; and *Lactobacillus debrueckii* subsp. *bulgaricus* which is capable of generating 0.4 g/L or more of D-lactic acid in the fermented substance when soy milk is inoculated with the strain and the same *Streptococcus thermophilus* above simultaneously and cultured.

In addition, the present invention provides (2) a lactic acid bacteria mixture starter including: *Streptococcus thermophilus* which is capable of accumulating 0.4 g/L or more of fructose in the fermented substance when soy milk is inoculated with the strain and cultured; and *Lactobacillus debrueckii* subsp. *bulgaricus* which is capable of generating 0.4 g/L or more of D-lactic acid in the fermented substance when soy milk is inoculated with the strain and the same *Streptococcus thermophilus* above simultaneously and cultured.

Effect of the Invention

According to the present invention, there can be provided a soy milk fermented substance with an excellent taste and flavor or physicality identical to that of yogurt obtained by fermenting cow milk with lactic acid bacteria without applying processing treatment such as enzyme treatment or extraction treatment to soy milk which is a material and without adding a material such as a sugar source, even in a case where only *Streptococcus thermophilus* and *Lactobacillus delbrueckii* subsp. *bulgaricus* are employed as a lactic acid bacteria mixture starter while a fermented substance employing soy milk is employed as a material. The yogurt-like soy milk fermented substance of the present invention does not make one feel an unpleasant odor peculiar to a soybean fermented substance and thus it is possible to anticipate that the product is widespread as a healthy material having an excellent function generated by a synergetic effect of soybean and lactic acid bacteria.

MODE FOR CARRYING OUT THE INVENTION

Figure 1:
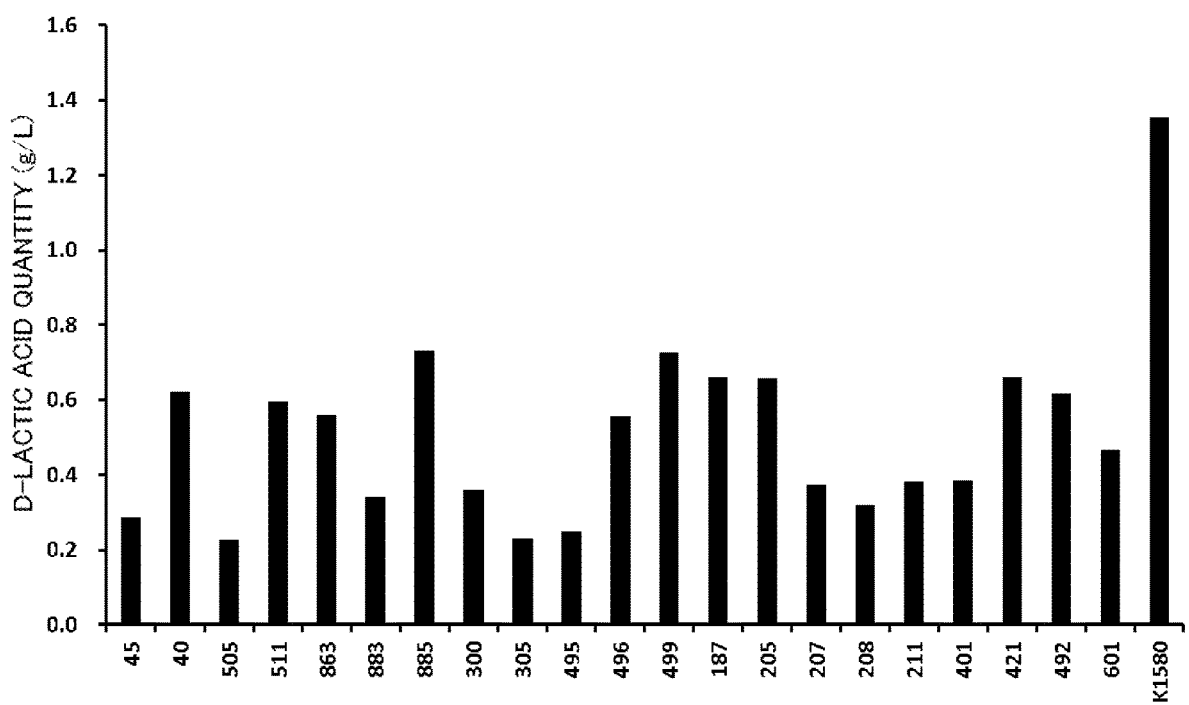
FIG. 1 is a graph depicting D-lactic acid quantity in a soy milk fermented substance obtained by mixing of a bred *Lactobacillus debrueckii* subsp. *bulgaricus* (K1581 strain) and a *Streptococcus thermophilus* strain isolated and selected from the commercially available mixture starter or the bred *Streptococcus thermophilus* strain (K1580 strain) with each other, inoculating the mixture in soy milk, and carrying out fermentation at the temperature of 42 degrees Centigrade for 24 hours.

Hereinafter, the present invention will be described in detail.

A soy milk fermented substance of the present invention is obtained by carrying out fermentation with only two bacterial species of lactic acid bacteria, Streptococcus thermophilus and Lactobacillus debrueckii subsp. bulgaricus without applying special processing treatment such as enzyme treatment to soy milk.

As soy milk used in the present invention, any kind of soy milk may be used as long as it is obtained by a conventional method, or alternatively, commercially available soy milk may be used. For example, it is possible to use the liquor obtained by boiling and milling the soy obtained by immersing and swelling exfoliated soybean or defatted soybean, and it is more preferable that the liquor obtained by removing soybean fiber from the liquor be used from the viewpoint of taste or texture. Further, the liquor obtained by dissolving whole-grain soy flour, defatted soy flour or the like may be employed. Although, in the JAS standard, 8.0% or more of soybean solid content is defined as soy milk, pure soy milk is defined at 6.0% or more, and soy milk drink is defined at 4.0% or more, the soybean solid content quantity is not limited in particular.

Streptococcus thermophilus used in the present invention can be grown in soy milk, and it is required to have a property of decomposing sucrose in soy milk and then producing glucose and fructose in a case where the Streptococcus thermophilus is solely grown in soy milk, and among them, accumulating fructose at a concentration of 0.4 f/L or more.

Although Lactobacillus debrueckii subsp. bulgaricus is not capable of assimilating sucrose included in soy milk as a sugar source, Streptococcus thermophilus decomposes sucrose into glucose and fructose, whereby they are assimilated and then Lactobacillus debrueckii subsp. bulgaricus can also be grown.

Although Streptococcus thermophilus takes the decomposed product as a sugar source while decomposing sucrose, if a strain with a high decomposition capability is particularly selected the sugar that is decomposed in the fermented substance is accumulated. In addition, in the soy milk fermented substance in which the quantity of the thus accumulated fructose exceeds 0.4 g/L, Lactobacillus debrueckii subsp. bulgaricus is well grown, and is capable of playing a significant role in producing a variety of metabolites and forming a taste and flavor of yogurt in the growing process.

Thus, although metabolism of Lactobacillus debrueckii subsp. bulgaricus is important in fermenting soy milk like yogurt, D-lactic acid produced by that metabolism is not produced in Streptococcus thermophilus that produces only L-lactic acid, and therefore, the D-lactic acid can be utilized as an easily measurable index indicative of metabolic activity of Lactobacillus debrueckii subsp. bulgaricus. In the present invention, it was found out that a fermented substance characterized in that 0.4 g/L or more of D-lactic acid quantity is accumulated therein improves a taste and flavor in particular as a result of Lactobacillus debrueckii subsp. bulgaricus has actively producing the metabolite.

The lactic acid bacteria having the above property can be selected from the lactic acid bacteria employed in making yogurt from milk or the same strain of lactic acid bacteria in the environment. In a case where lactic acid bacteria are bred, all of means which are generally widely employed can be utilized. For example, induction of mutation employing ultraviolet ray or induction of mutation employing pharmaceutics, subculture on a medium consisting essentially of soy milk or the like, it is possible to obtain Streptococcus thermophilus which accumulates 0.4 g/L or more of fructose in soy milk or Lactobacillus debrueckii subsp. bulgaricus indicative of high D-lactic acid production quantity of 0.4 g/L or more in soy milk when they are cultured simultaneously.

Upon breeding lactic acid bacteria, a strain with a high acid production capability can be bred by simultaneously inoculating Streptococcus thermophilus and Lactobacillus debrueckii subsp. bulgaricus and then carrying out fermentation at the fermentation temperature of 30 to 45 degrees Centigrade, more preferably at the fermentation temperature of 32 to 42 degrees Centigrade and for the fermentation time of 4 to 24 hours.

Although the lactic acid bacteria that produces D-lactic acid is Lactobacillus debrueckii subsp. bulgaricus, the bacteria cannot assimilate sucrose which consists essentially of sugar in soy milk and thus the bacteria cannot be grown solely, and may be killed. On the other hand, the Inventor, et al., found out that, in many cases, Streptococcus thermophilus is capable of assimilating and grow sucrose to some extent in soy milk, and at that juncture, the lactic acid bacteria decomposes sucrose, whereby glucose and fructose are produced, and if Lactobacillus debrueckii subsp. bulgaricus is caused to coexist, they are assimilated, and can be gradually grown.

Although it is considered that sugar is added to soy milk and complimented in order to grow Lactobacillus debrueckii subsp. bulgaricus, there may be a case in which a sufficient quantity of D-lactic acid generation is not indicated merely by complimenting sugar, and compatibility of two strains other than a complimentary relationship of sugar exists and thus it is important to select Lactobacillus debrueckii subsp. bulgaricus with active metabolism which is capable of producing 0.4 g/L or more as D-lactic acid quantity at the time of culture with Streptococcus thermophilus which accumulates fructose.

By selecting or breeding a combination of appropriate strains from among a number of the existing Streptococcus thermophilus and Lactobacillus debrueckii subsp. bulgaricus, both bacterial species are activated in soy milk and it is possible to form a good taste and flavor or physicality like yogurt; and however, Streptococcus thermophilus actively assimilates sucrose, and as a result, L-lactic acid to be produced by the bacteria is also produced in the fermented substance.

In order to obtain a soy milk fermented substance like yogurt, it is necessary to include L-lactic acid produced by Streptococcus thermophilus as well as D-lactic acid.

The lactic acid bacteria employed in the present invention can be obtained by selection or breeding as described above, and Examples of the present specification include: a combination of Streptococcus thermophilus K1580 strain and Lactobacillus debrueckii subsp. bulgaricus K1581 strain; a combination of Streptococcus thermophilus K1584 strain and Lactobacillus debrueckii subsp. bulgaricus K1585 strain; and a combination of *Streptococcus thermophilus* strain available from Danisco Inc. (the strain isolated from the mixture starter YO-MIX499) and *Lactobacillus debrueckii* subsp. *bulgaricus* strain available from Danisco Inc. (the strain isolated from the mixture starter YO-MIX505, 511, 863) or the like. The soy milk fermented substance of the present invention can be obtained by using the lactic acid bacteria having the above properties, and the product is not limited to the strains described in Examples.

A method for fermenting soy milk with a lactic acid bacteria can be carried out on the basis of a method for making generally known yogurt or lactic acid bacteria drink; for example, it is sufficient that *Streptococcus thermophilus* is inoculated in soy milk so as be $1\times10^4$ to $1\times10^8$ cfu/mL, more preferably $1\times10^5$ to $1\times10^7$ cfu/mL, and *Lactobacillus debrueckii* subsp. *bulgaricus* is inoculated in soy milk so as to be $1\times10^2$ to $1\times10^7$ cfu/mL, more preferably $1\times10^3$ to $1\times10^5$ cfu/mL, and fermentation is carried out at a fermentation temperature of 30 to 45 degrees Centigrade, more preferably 37 to 42 degrees Centigrade and in a range of 4 to 24 hours, and the fermentation mode is not limited in particular.

The thus obtained yogurt-like soy milk fermented substance of the present invention is characterized by including 0.4 g/L or more of D-lactic acid, metabolisms of *Streptococcus thermophilus* and *Lactobacillus debrueckii* subsp. *bulgaricus* both becomes active, thereby indicating the lactic acid production quantity that has not been obtained up to now, in a case where a commercially available lactic acid bacteria mixture starter is employed as it is, resulting in a soy milk fermented substance with a yogurt-like favor or good physicality, having aroma components derived from the respective bacterial species. In addition, it is possible to carry out fermentation without adding a material other than a soybean-derived material and thus the product is not influenced by an auxiliary material-derived taste. Further, the soy milk fermented substance of the present invention has a high versatility, and can be applied to any product of a soybean-related drink or food such as seasoning or cheese and drink aspect as well as yogurt-like food.

Although the embodiment described an example of making a lactic acid fermented product by employing only two bacterial species of *Streptococcus thermophilus* and *Lactobacillus debrueckii* subsp. *bulgaricus*, the present invention is not limited thereto, and in addition to the two species of lactic acid bacteria shown in the present invention, there may be concurrently used a lactic acid bacteria other than *Streptococcus thermophilus* and *Lactobacillus debrueckii* subsp. *bulgaricus* as long as it does not influence lactic acid fermentation of *Streptococcus thermophilus* and *Lactobacillus debrueckii* subsp. *bulgaricus* or the flavor of the obtained soy milk fermented substance.

Hereinafter, the present invention will be further specifically described by way of examples. It is to be noted that the technical scope of the present invention is not limited by these examples.

EXAMPLES

1. Measurement of D-Lactic Acid Quantity of Soy Milk Fermented Substance Employing Commercially Available Lactic Acid Bacteria Mixture Starter (1) Lactic Acid Bacteria Mixture Starter As lactic acid bacteria mixture starters, there were used commercially available lactic acid bacteria mixture starters for making yogurt (available from Danisco Inc., freeze-dried products including both strains of *Streptococcus thermophilus* and *Lactobacillus debrueckii* subsp. *bulgaricus*. Hereinafter, these products may be occasionally referred to as "commercially available mixture starter"). As to these commercially available mixture starters, a variety of products exist according to the properties of the *Streptococcus thermophilus* strain and the*Lactobacillus debrueckii* subsp. *bulgaricus* strain. Specifically, the above starters include: YO-MIX300, YO-MIX305, YO-MIX496, YO-MIX499, YO-MIX505, YO-MIX511, YO-MIX863, YO-MIX883, YO-MIX885, YO-MIX401, YO-MIX421, YO-MIX495, YO-MIX601 (wherein all the assigned numbers designate product numbers).

(2) Fermentation Condition and Measurement Method

As soy milk source liquor, commercially available unadjusted pure soy milk (available from Kokkoman Soy Foods Corporation) was employed. On the other hand, the freeze-dried product of each lactic acid bacteria mixture starter was cultured in 10 mL of an LM17 culture medium (Terzaghi and Sandine, Appl. Microbiol. 29, 807 to 813, 1975), and the culture liquor was centrifuged and washed with 0.9% NaCl solution and then were suspended again in 10 mL of 0.9% NaCl solution. The thus formulated suspension was inoculated by 1.0% (v/v) in the soy milk fermented source liquor mentioned above, and fermentation was carried out at the temperature of 42 degrees Centigrade and for 24 hours. Subsequently, the fermentation completed after the elapse of 24 hours, and D-lactic acid quantity in the soy milk fermented substance was measured by an enzyme electrode approach (available from Oji Scientific Instruments, Biosensor BF-5).

(3) Result

Figure 4:
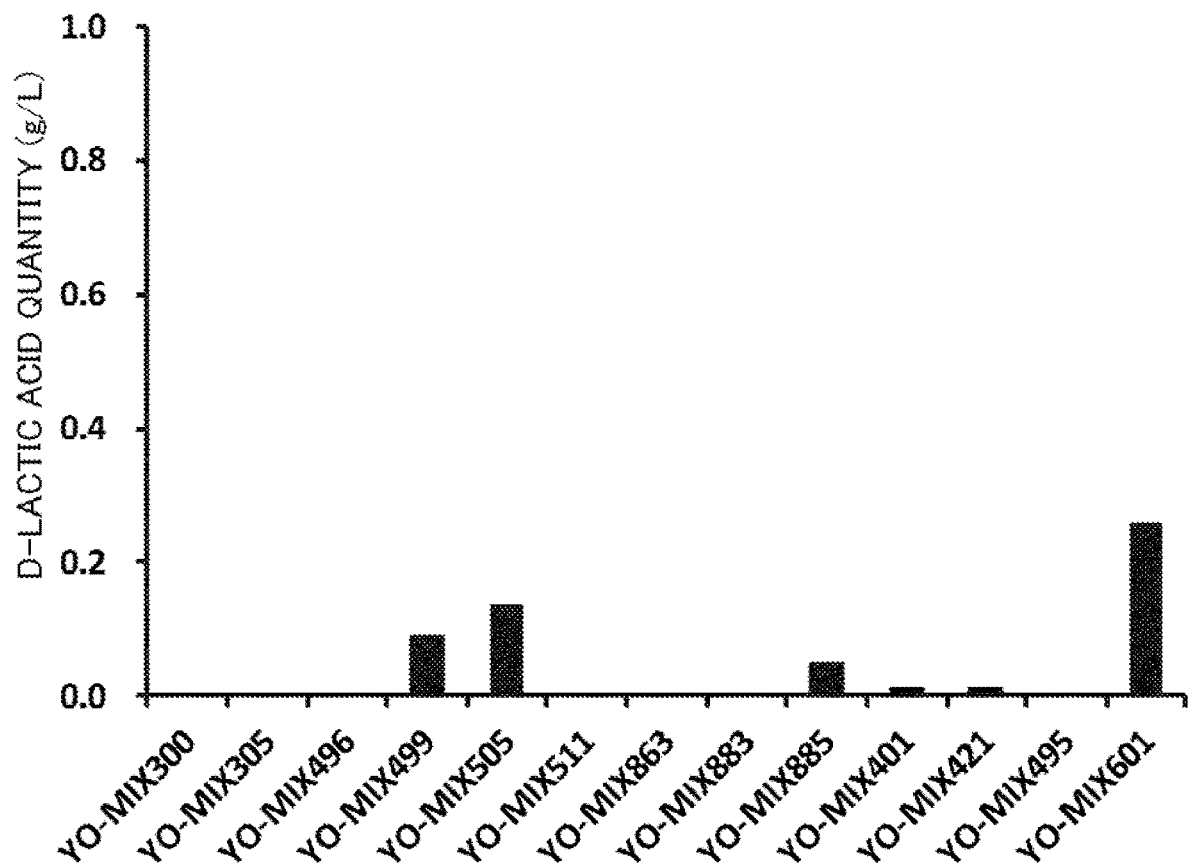
FIG. 4 is a graph depicting D-lactic acid quantity in a soy milk fermented substance obtained by fermenting (at the temperature of 42 degrees Centigrade for 24 hours) only the commercially available mixture starters for which breeding or isolating operation or selecting operation or the like is not carried out (a mixture starter of *Streptococcus thermophilus* and *Lactobacillus debrueckii* subsp. *bulgaricus*).

The result is shown in FIG. 4. When D-lactic acid quantity in the soy milk fermented substance obtained by carrying out fermentation for 24 hours was measured, it was verified that D-lactic acid is hardly produced, and a soy milk fermented substance having a desired yogurt-like flavor is not obtained (FIG. 4).

Isolation, selection, and breeding of sampled strains (1) *Streptococcus thermophilus*

From the commercially available starters (each of which includes two bacterial species of *Streptococcus thermophilus* and *Lactobacillus debrueckii* subsp. *bulgaricus*), only the *Streptococcus thermophilus* strains were isolated. The isolated strains, on the basis of the product numbers of the commercially available starters, were: *Streptococcus thermophilus* 45 stain; St. 40 strain; St. 505 strain; St. 511 strain; St. 863 strain; St. 883 strain; St. 885 strain; St. 300 strain; St. 305 strain; St. 495 strain; St. 496 strain; St. 499 strain; St. 187 strain; St. 205 strain; St. 207 strain; St. 208 strain; St. 211 strain; St. 401 strain; St. 421 strain; St. 492 strain; St. 601 strain.

Among the isolated strains mentioned above, the inoculum of the isolated bacteria strains were inoculated in soy milk at a rate of 1%, and when culture was carried out at the temperature of 37 to 45 degrees Centigrade and for 12 to 24 hours, *Streptococcus thermophilus* strains which are capable of accumulating 0.4 g/L or more of fructose were selected in the fermented substance and then were employed as the selected strains. Specifically, *Streptococcus thermophilus* (St.) 40 strain, St. 511 strain, St. 863 strain, St. 885 strain, St. 496 strain, St. 499 strain, St. 187 strain, St. 205 strain, St. 401 strain, St. 421 strain, St. 492 strain, St. 601 strain were employed as the selected strains.

In addition, *Streptococcus thermophilus* St. 2333 stain and *Lactobacillus debrueckii* subsp. *bulgaricus* Lb. 185 strain owned by NIZO food research corporation based on Holland were inoculated in pure soy milk (available from Kikkoman Soy Foods Corporation), and subculture was carried out. The soy milk fermented substance was repeatedly inoculated in soy milk at a rate of 1% (v/v), and culture was carried out at the temperature of 37 to 45 degrees Centigrade and for 12 to 24 hours. Subculture was carried out as to approximately 700 generations, and the *Streptococcus thermophilus* strain isolated from the obtained soy milk fermented substance were employed as K1580 strain.

Further, *Streptococcus thermophilus* St. 131 stain and *Lactobacillus debrueckii* subsp. *bulgaricus* Lb. 194 strain similarly owned by NIZO food research corporation were inoculated in pure soy milk (available from Kokkoman Soy Foods Corporation), and subculture was carried out. The soy milk fermented substance was repeatedly inoculated in soy milk at a rate of 1% (v/v), and subculture was carried out at the temperature of 37 to 45 degrees Centigrade and for 12 to 24 hours. Subculture was carried out as to approximately 700 generations, and the *Streptococcus thermophilus* strain isolated from the obtained soy milk fermented substance were employed as K1584 strain.

(2) *Lactobacillus debrueckii* subsp. *bulgaricus*

From the commercially available starters mentioned above, only *Lactobacillus debrueckii* subsp. *bulgaricus* strains were isolated. The isolated strains, on the basis of the product numbers of the commercially available starters, were: *Lactobacillus debrueckii* subsp. *bulgaricus*, Lb. 300 strain; Lb. 305 strain; Lb. 401 strain; Lb. 421 strain; Lb. 492 strain; Lb. 495 strain; Lb. 496 strain; Lb. 499 strain; Lb. 505 strain; Lb. 511 strain; Lb. 601 strain; Lb. 863 strain; Lb. 883 strain; Lb. 885 strain.

Among the isolated strains mentioned above, together with the 1.0% of the selected strains of *Streptococcus thermophilus* described above, 1.0% of the inoculum of the above isolated strains was inoculated in soy milk, and when culture was carried out at the temperature of 37 to 45 degrees Centigrade and for 12 to 24 hours, the *Lactobacillus debrueckii* subsp. *bulgaricus* strains that accumulate 0.4 g/L or more of D-lactic acid in the fermented substance were selected, and were employed as the selected strains. Specifically, *Lactobacillus debrueckii* subsp. *bulgaricus* (Lb.) 492 strain, Lb. 505 strain, Lb. 511 strain, Lb. 601 strain, were employed as the selected strains.

In addition, *Streptococcus thermophilus* St. 2333 stain and *Lactobacillus delbruekii* subsp. *bulgaricus* Lb. 185 strain owned by NIZO food research corporation were inoculated in pure soy milk (available from Kikkoman Soy Foods Corporation), and subculture was carried out. The soy milk fermented substance was repeatedly inoculated in soy milk at a rate of 1% (v/v), and culture was carried out at the temperature of 37 to 45 degrees Centigrade and for 12 to 24 hours. Subculture was carried out as to approximately 700 generations, and the *Lactobacillus debrueckii* subsp. *bulgaricus* strain isolated from the obtained soy milk fermented substance were employed as K1581 strain.

Further, *Streptococcus thermophilus* St. 131 stain and *Lactobacillus debrueckii* subsp. *bulgaricus* Lb. 194 strain similarly possessed by NIZO food research corporation were inoculated in pure soy milk (available from Kokkoman Soy Foods Corporation), and subculture was carried out. The soy milk fermented substance was repeatedly inoculated in soy milk at a rate of 1% (v/v), and culture was carried out at the temperature of 37 to 45 degrees Centigrade and for 12 to 24 hours. Subculture was carried out as to approximately 700 generations, and the *Lactobacillus debrueckii* subsp. *bulgaricus* strain isolated from the obtained soy milk fermented substance were employed as K1585 strain. Similarly, the *Lactobacillus debrueckii* subsp. *bulgaricus* strain isolated from the subculture of St. 131 and Lb. 185 was employed as K1583 strain.

3. Comparison of D-Lactic Acid Quantity in Soy Milk Fermented Substance (1) Sampled Strains Soy milk was fermented by employing the lactic acid bacteria isolated from the commercially available mixture starters and the selected and bred lactic acid bacteria (refer to item 2 above), and D-lactic acid quantities in the obtained soy milk fermented substance were measured and compared with each other.

(2) Fermentation Condition and Measurement Method

As a fermentation material, pure soy milk (commercially available from Kikkoman Soy Foods Corporation) was employed. To this fermentation material, a composition of the lactic acid bacteria mixture starter made of the *Streptococcus thermophilus* strains and the *Lactobacillus debrueckii* subsp. *bulgaricus* strain was added, and fermentation was carried out at the temperature of 42 degrees Centigrade and for 24 hours. After the fermentation had completed, D-lactic acid quantity in the obtained soy milk fermented substance was measured by the enzyme approach (available from Oji Scientific Instruments, Biosensor BF-5).

(3) Result

FIG. 1 is a graph depicting a result obtained by measuring D-lactic acid quantity in a soy milk fermented substance obtained by carrying out fermentation, presupposing that a lactic acid bacteria mixture starter is composed of a variety of *Streptococcus thermophilus* strains; and the *Lactobacillus debrueckii* subsp. *bulgaricus* K1581 strain that is a bred strain.

Figure 2:
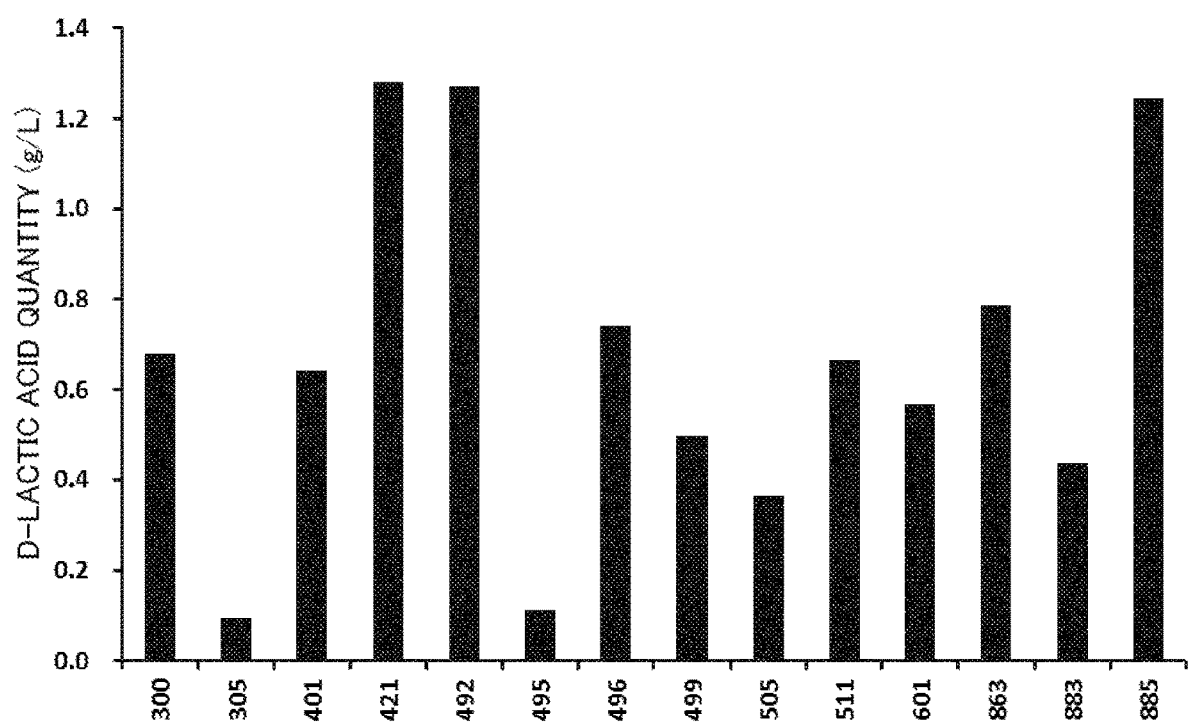
FIG. 2 is a graph depicting D-lactic acid quantity in the soy milk fermented substance obtained by mixing the bred *Lactobacillus debrueckii* subsp. *bulgaricus* (K1585 strain) and the *Streptococcus thermophilus* strains isolated and selected from the commercially available mixture starter with each other, inoculating the mixture in soy milk, and carrying out fermentation at the temperature of 42 degrees Centigrade and for 24 hours.

FIG. 2 is a graph depicting a result obtained by measuring D-lactic acid quantity in a soy milk fermented substance obtained by fermenting soy milk on a similar condition, presupposing that the *Lactobacillus debrueckii* subsp. *bulgaricus* K1585 strain that is a bred strain is employed similarly as a lactic acid bacteria mixture starter in place of the *Lactobacillus debrueckii* subsp. *bulgaricus* K1581 strain.

As shown in FIG. 1 and FIG. 2, even if the *Lactobacillus debrueckii* subsp. *bulgaricus* strains are identical to each other, D-lactic acid production quantities are different from each other depending on the *Streptococcus thermophilus* strains that are combined with each other; and therefore, it was verified that metabolic capabilities of the *Lactobacillus debrueckii* subsp. *bulgaricus* strains vary depending on the characteristics of the *Streptococcus thermophilus* strains. In particular, in the strains selected on the basis of an index indicating that the production quantity of fructose becomes 0.4 g/L or more, D-lactic acid production quantity was prone to significantly increase.

Figure 3:
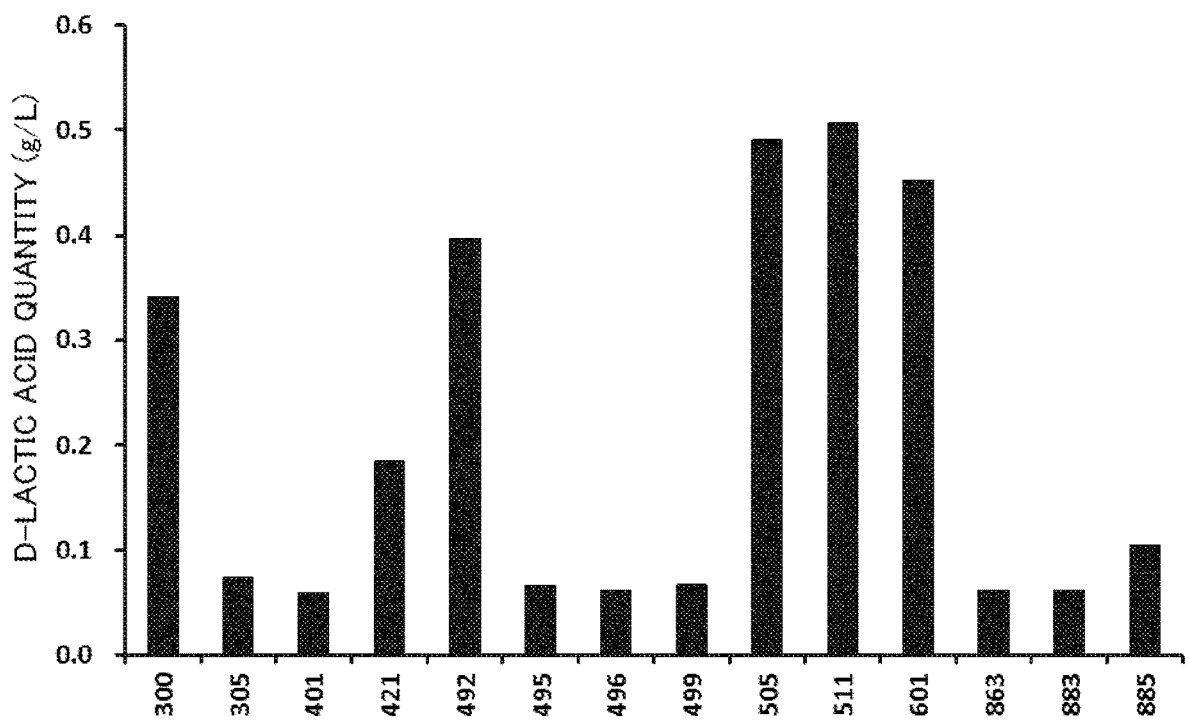
FIG. 3 is a graph depicting D-lactic acid quantity in a soy milk fermented substance obtained by mixing culture of the bred *Streptococcus thermophilus* strain (K1580 strain) and the *Lactobacillus debrueckii* subsp. *bulgaricus* strains isolated from the commercially available mixture starters, inoculating the mixture in soy milk, and carrying out fermentation at the temperature of 42 degrees Centigrade for 24 hours.

FIG. 3 is a graph depicting a result obtained by D-lactic acid quantity in a soy milk fermented substance obtained by carrying out fermentation on a similar condition, presupposing that a lactic acid bacteria mixture starter is composed of; the *Streptococcus thermophilus* K1580 strain that is a bred strain; and each of the *Lactobacillus debrueckii* subsp. *bulgaricus* strains isolated from a commercially available starter, and then, the starter is inoculated in soy milk.

As shown in FIG. 3, even in a case where the bred *Streptococcus thermophilus* K1580 strain was used, it was verified that there is a significant difference in production of the D-lactic acid quantity depending on the *Lactobacillus debrueckii* subsp. *bulgaricus* strain.

As shown in FIG. 1, FIG. 2, FIG. 3, and FIG. 4, D-lactic acid is not produced so much in the soy milk fermented substance obtained by carrying out fermentation while the commercially available lactic acid bacteria mixture starter is employed as it is, in the *Streptococcus thermophilus* strains and the *Lactobacillus debrueckii* subsp. *bulgaricus* strains, whereas the starter is substituted by the strains obtained by selecting and breeding both of the *Streptococcus thermophilus* strains and the *Lactobacillus debrueckii* subsp. *bulgaricus* strains, whereby a soy milk fermented substance including 0.4 g/L or more of D-lactic acid can be obtained. In particular, in a case where a lactic acid bacteria mixture starter composed of; lactic acid bacteria (the *Streptococcus thermophilus* strain K1580 strain and the *Lactobacillus debrueckii* subsp. *bulgaricus* K1581 strain) that are bred in the present invention, a soy milk fermented substance with a further large quantity of D-lactic acid can be obtained (refer to FIG. 1).

In the light of the above result, it was verified that a significant change arises in D-lactic acid production quantity generated by *Lactobacillus debrueckii* subsp. *bulgaricus* strain fermented together with the characteristics that *Streptococcus thermophilus* has, and D-lactic acid production quantity in soy milk is significantly different depending on the strain in *Lactobacillus debrueckii* subsp. *bulgaricus* as well.

4. Comparison of D-Lactic Acid Quantity After Fermentation With *Lactobacillus debrueckii* subsp. *bulgaricus* Strains in Pure Soy Milk Film Permeate (1) As described above, it was found that D-lactic acid production quantity generated by the *Lactobacillus debrueckii* subsp. *bulgaricus* strains significantly varied depending on the characteristics of the characteristics of the *Streptococcus thermophilus* strains. Therefore, in order to verify a difference in metabolic capability while in soy milk film permeation of the selected and bred *Lactobacillus debrueckii* subsp. *bulgaricus* strains and *Lactobacillus debrueckii* subsp. *bulgaricus* strains that are isolated from the commercially available starter, D-lactic acid production quantities in the soy milk film permeate obtained by complementing fructose as sugar in advance were compared with each other. The soy milk film permeate is obtained by removing inactive protein or lipid with high polymer from soy milk, and it is considered that there are not so significant differences between free amino acids in soy milk, insoluble peptide, sugar content or mineral or the like.

(2) Formulating Pure Soy Milk Film Permeate

Commercially available pure soy milk was suctioned (−60 kPa) by a vacuum pump employing a hollow fiber-shaped ultrafiltration module (model: USP-143 (available from Asahi Kasei Corporation)), and the liquor permeating the film was employed as a pure soy milk permeate. To this liquor, fructose was aseptically added to obtain final concentration of 1.0% (v/v) (pure soy milk film permeate). Further, hydrochloric acid was added to this soy milk film permeate, and an acidic soy milk film permeate adjusted to pH 5.0 was formulated.

(3) Measurement of D-lactic Acid Production Quantity After Culture in Soy Milk Film Permeate The *Lactobacillus debrueckii* subsp. *bulgaricus* strains isolated from the commercially available flour mixture starters for making yogurt (available from Danisco Inc., Freeze-dried products including bred *Streptococcus thermophilus* strains and *Lactobacillus bulgaricus* strains); the bred three strains of *Lactobacillus debrueckii* subsp. *bulgaricus* strains (K1581 strain, K1583 strain, K1585 strain); and a wild-type strain (ATCC11842 strain) were respectively cultured in MRS culture mediums. The obtained bacteria liquor from the viewpoint of was centrifuged and washed with 0.85% sterilization saline two times, the obtained pellet was suspended in pure soy milk film permeate, and the permeate was employed as a starter bacteria liquor.

Figure 5:
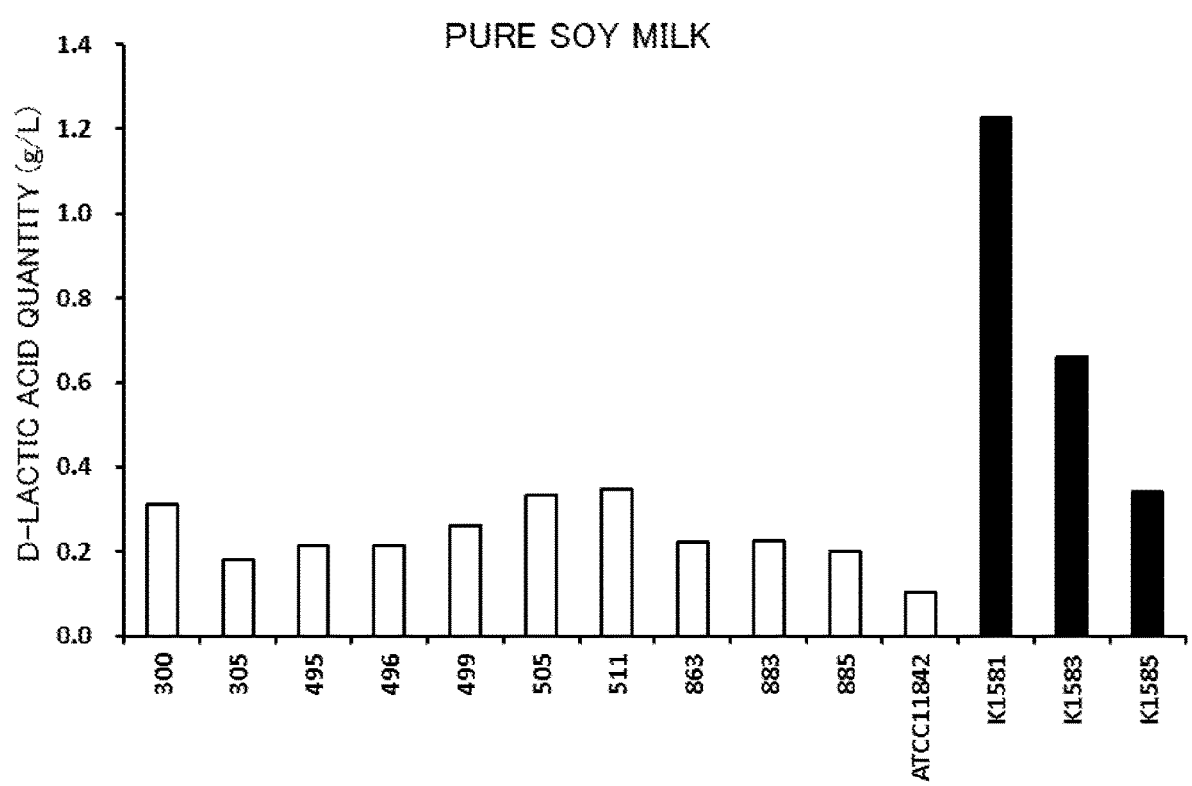
FIG. 5 is a measurement diagram of D-lactic acid production quantity in a fermentation liquor obtained by fermenting a soy milk film permeate obtained by adding 1/0% (w/v) of fructose in a permeate obtained by permeating pure soy milk with an MF ultrafiltration film, at the temperature of 42 degrees Centigrade for 24 hours, solely with *Lactobacillus debrueckii* subsp. *bulgaricus*.
Figure 6:
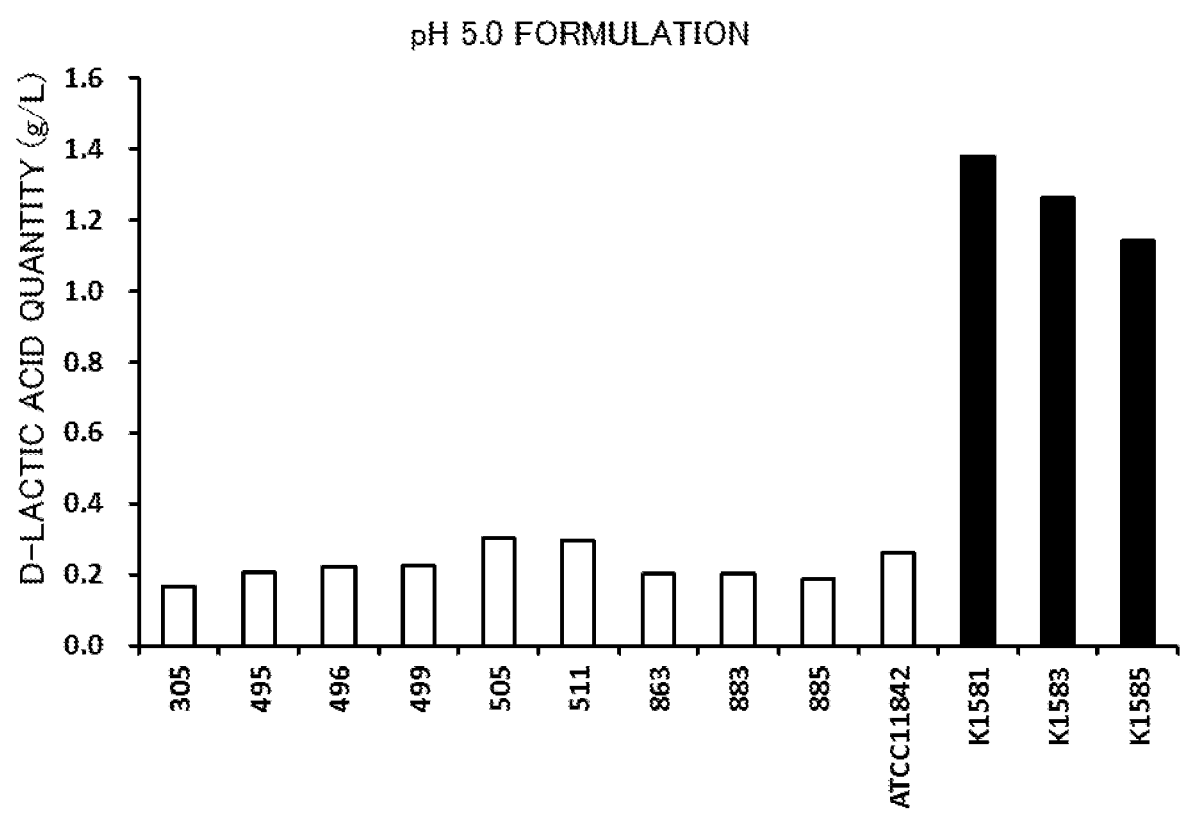
FIG. 6 is a measurement diagram of D-lactic acid production quantity in a fermentation liquor obtained by fermenting an acidic soy milk film permeate obtained by adding 1.0% (w/v) of fructose in a permeate obtained by permeating pure soy milk in the MF ultrafiltration film and adjusting pH to 5.0, and fermented solely with *Lactobacillus debrueckii* subsp. *bulgaricus*.

The bacteria liquor washed and sterilized in a respective one of the pure soy milk film permeate and acidic (pH 5.0) soy milk film permeate was inoculated by 1.0% and cultured at the temperature of 42 degrees Centigrade and for 24 hours (the *Lactobacillus debrueckii* subsp. *bulgaricus* strains were cultured solely), and D-lactic acid quantity of the bacteria liquor after cultured was measured (FIG. 5 and FIG. 6).

In the pure soy milk film permeate, in comparison with the commercially available starters or ATCC11842 strain, D-lactic acid production quantity generated by the *Lactobacillus debrueckii* subsp. *bulgaricus* strains bred in the present invention indicated a high value. Similarly, in the acidic soy milk film permeate, in comparison with pure soy milk film permeate, it was observed that there is a significant difference in D-lactic acid production quantity between the commercially available starters and the bred strains. In the *Lactobacillus debrueckii* subsp. *bulgaricus* strains isolated from the commercially available starter, in particular, on a low pH condition (pH 5.0), it was verified that the production quantity of D-lactic acid is low, whereas the bred strains produce D-lactic acid that is three times or more in quantity on the same condition. In co-fermentation with the *Streptococcus thermophilus* strains in soy milk, it is considered that pH lowers earlier due to growth of the *thermophilus* strains, and subsequently, the *Lactobacillus debrueckii* subsp. *bulgaricus* strains grow. In the commercially available *Lactobacillus debrueckii* subsp. *bulgaricus* strains, it was verified that, in the environment as described above, no strain exceeding 0.4 (g/L) in production of D-lactic acid exists, and growth and metabolism are limited in the soy milk environment. In addition to the above result, with respect to the bred strains, even on the low pH and soy milk environments as well, in comparison with the commercially available strains or ACTT11842 strain, it is estimated that metabolism arises very actively, and as a result, it is considered to be possible to make a soy milk fermented substance with a yogurt-like acidic taste or flavor.

Incidentally, the isolated strains derived from the commercially available starter include a strain obtained by producing 0.4 g/L or more of D-lactic acid as a selected strain in FIG. 3, such as Lb. 505 strain or Lb. 511 strain, and in FIG. 5 and FIG. 6 as well, these strains indicate higher F-lactic acid production than that of the strains derived from any other commercially available starter; and however, the production quantity of 0.4 g/L is not obtained. It is considered that this is because no *Streptococcus thermophilus* exists in the tests shown in FIG. 5 and FIG. 6. Although fructose is complemented as sugar in pure soy milk film permeate, it is considered that *Streptococcus thermophilus* not only activates metabolism of *Lactobacillus debrueckii* subsp. *bulgaricus* and enhances the production quantity of D-lactic acid but also plays another role.

5. Measurement of Remaining Sugar Quantity of Fructose in Soy Milk Fermentation Liquor Obtained by Fermenting the *Thermophilus* Solely From the commercially available lactic acid bacteria mixture starters (available from Danisco Inc.), YO-MIX300, 305, 496, 499, 501, 885, only the *Streptococcus thermophilus* strains (St. 300 strain, St. 305 strain, St. 496 strain, ST. 499 strain, St. 501 strain, St. 885 strain) were isolated. Each of the isolated strains was cultured in the LM17 culture medium of 10 mL, and the culture liquor was centrifuged and washed with 0.9% NaCl solution and suspended again in 10 mL of 0.9% NaCl solution. As the soy milk fermentation source liquor, commercially available pure soy milk (available from Kikkoman Sot Foods Corporation) was employed. In this soy milk fermentation source liquor, the pure soy milk formulated as described above was inoculated by 1.0% (v/v), and fermentation was carried out at the temperature of 42 degrees Centigrade and for 24 hours. Subsequent to the fermentation, centrifuged supernatant was re-collected, and the remaining sugar quantity of fructose was measured by F kit D-glucose/fructose (available from JK International Corporation). The result is shown in FIG. 7.

Figure 7:
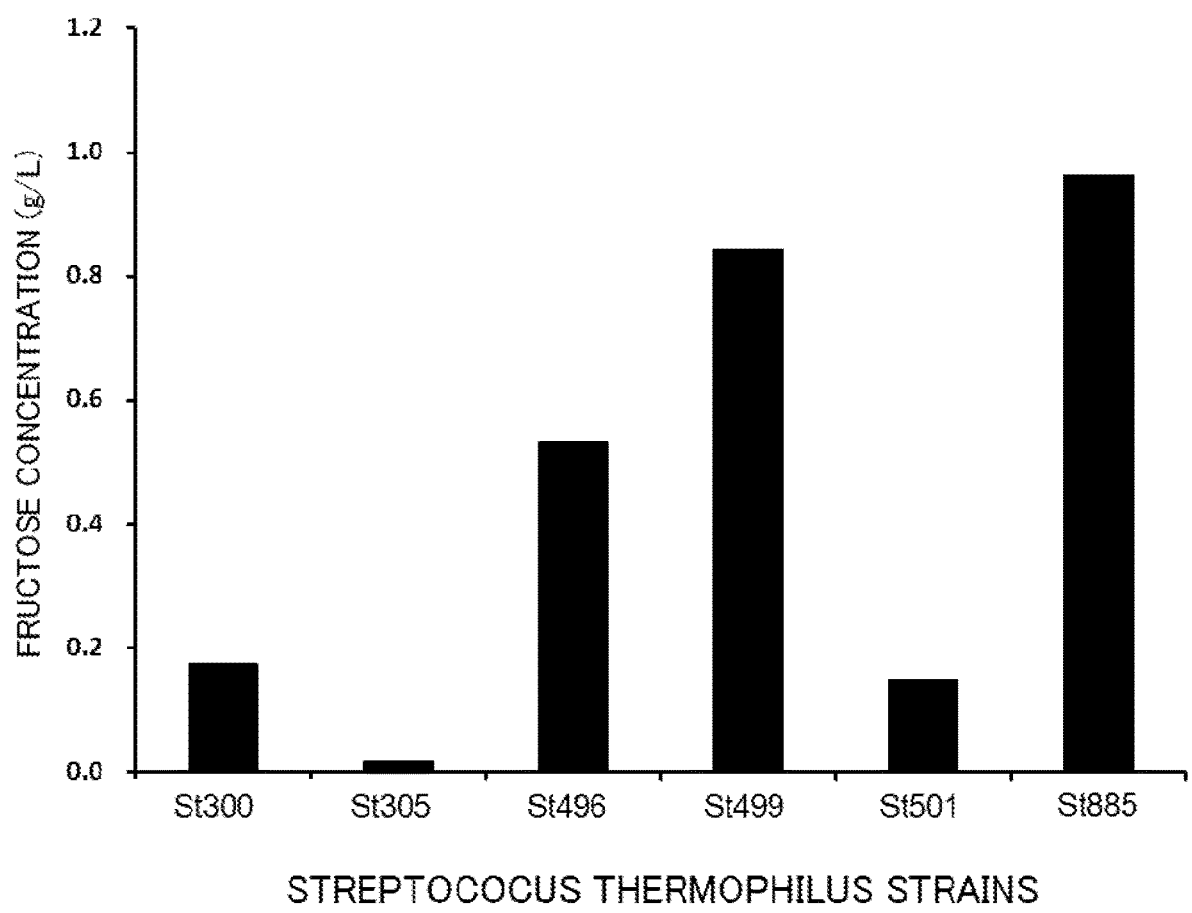
FIG. 7 is a measurement diagram of fructose concentration in a soy milk fermented substance obtained by fermenting, at the temperature of 42 degrees Centigrade for 24 hours, the *Streptococcus thermophilus* strain isolated from the commercially available mixture starters (the mixture starters of *Streptococcus thermophilus* and *Lactobacillus debrueckii* subsp. *bulgaricus*).

As shown in FIG. 7, it was found that among the *Streptococcus thermophilus* strains, there exist strains which accumulate 0.4 g/L or more of fructose in the soy milk fermented substance as is the case with St. 496 strain, St. 499 strain, St. 885 strain, and strains which do not accumulate so.

6. Influence on Production Of D-Lactic Acid Quantity According to Combination of Lactic Acid Bacteria Mixture Starters A lactic acid bacteria mixture starter combined, at 1:1, with the *Lactobacillus debrueckii* subsp. *bulgaricus* strains (Lb. 505 strain, Lb. 511 strain, Lb. 863 strain) obtained by isolating the *Streptococcus thermophilus* strain (St. 499) characterized by accumulating fructose and the strain (St. 305 strain) that does not accumulate so from the commercially available mixture starters YO-MIX505, 511, 863 was configured. This starter was added to commercially available pure soy milk (commercially available from Kikkoman Soy Foods Corporation), fermentation was carried out at the temperature of 42 degrees Centigrade and for 24 hours, and a soy milk fermented substance was obtained. After the fermentation had completed, D-lactic acid quantity in the obtained soy milk fermented substance was measured by the enzyme electrode approach (Oji Scientific Instruments, Biosensor BF-5).

Figure 8:
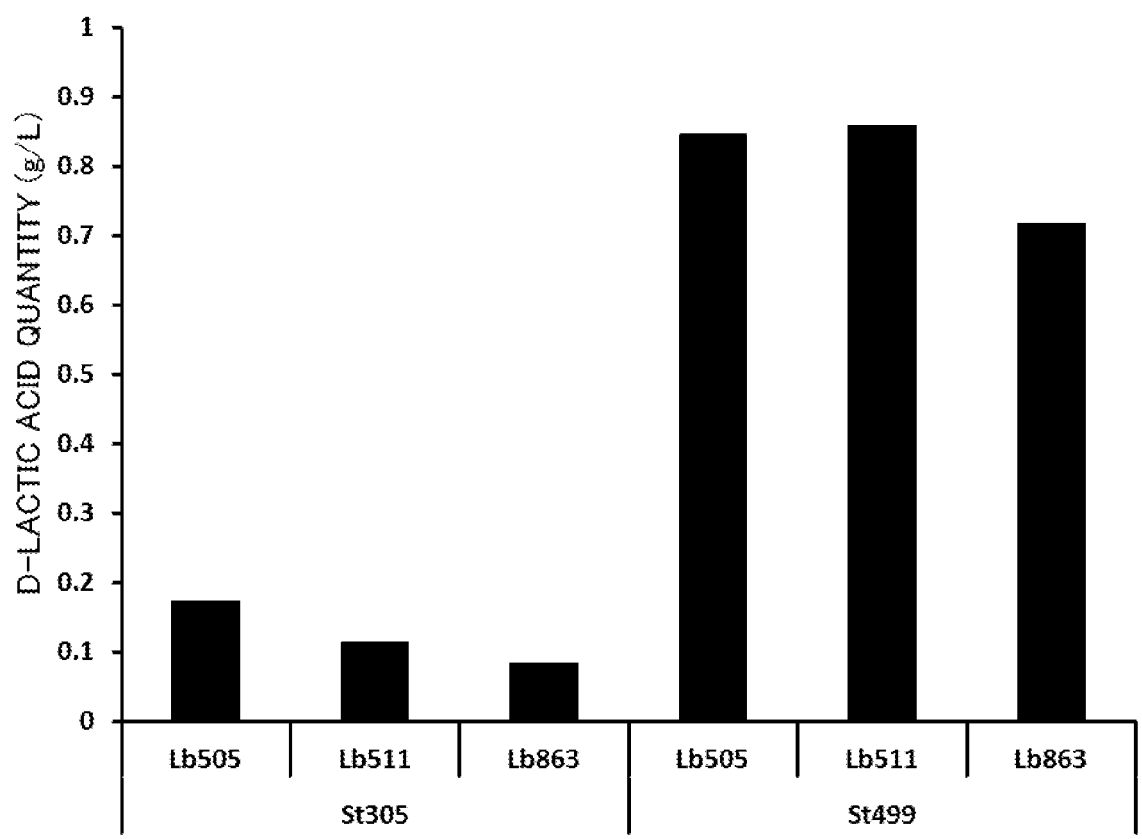
FIG. 8 is a measurement diagram of D-lactic acid production quantity in a soy milk fermented substance obtained by mixing, at a ratio of 1:1, the *Lactobacillus debrueckii* subsp. *bulgaricus* isolated from the commercially available mixture starters YO-MIX505, 511, 863 as is the case with the *Streptococcus thermophilus* strain isolated from the commercially available mixture starters YO-MIX305, 499, and carrying out fermentation at the temperature of 42 degrees Centigrade for 24 hours.

FIG. 8 shows a measurement result of D-lactic acid production quantity in the soy milk fermented substance. As shown in FIG. 8, in combination with the *Streptococcus thermophilus* strain that accumulates fructose, it was verified that 0.4 g/L or more of D-lactic acid is produced, and even if no auxiliary material is added, a symbiotic relationship with *Lactobacillus debrueckii* subsp. *bulgaricus* is established in soy milk as well.

7. Change of Sugar Concentration in Soy Milk Fermentation with Elapse of Time

In order to ensure that the *Streptococcus thermophilus* strain and the *Lactobacillus debrueckii* subsp. *bulgaricus* strain establish the symbiotic relationship in soy milk, it is considered to be indispensable that sucrose, which is a main sugar content of soy milk, is decomposed by the *Streptococcus thermophilus* strain and then fructose is accumulated to thereby supply a sugar source to the *Lactobacillus debrueckii* subsp. *bulgaricus* strain. In this occasion, the remaining sugar quantities of sucrose and fructose when the *Streptococcus thermophilus* K1580 strain was fermented solely and when the *Streptococcus thermophilus* K1580 strain and the *Lactobacillus debrueckii* subsp. *bulgaricus* K1581 strain were co-fermented were measured after the elapse of time. The fermentation temperature was set to 42 degrees Centigrade. A change of sucrose with the elapse of time is shown in FIG. 9, and a change of fructose with the elapse of time is shown in FIG. 10.

Figure 11:
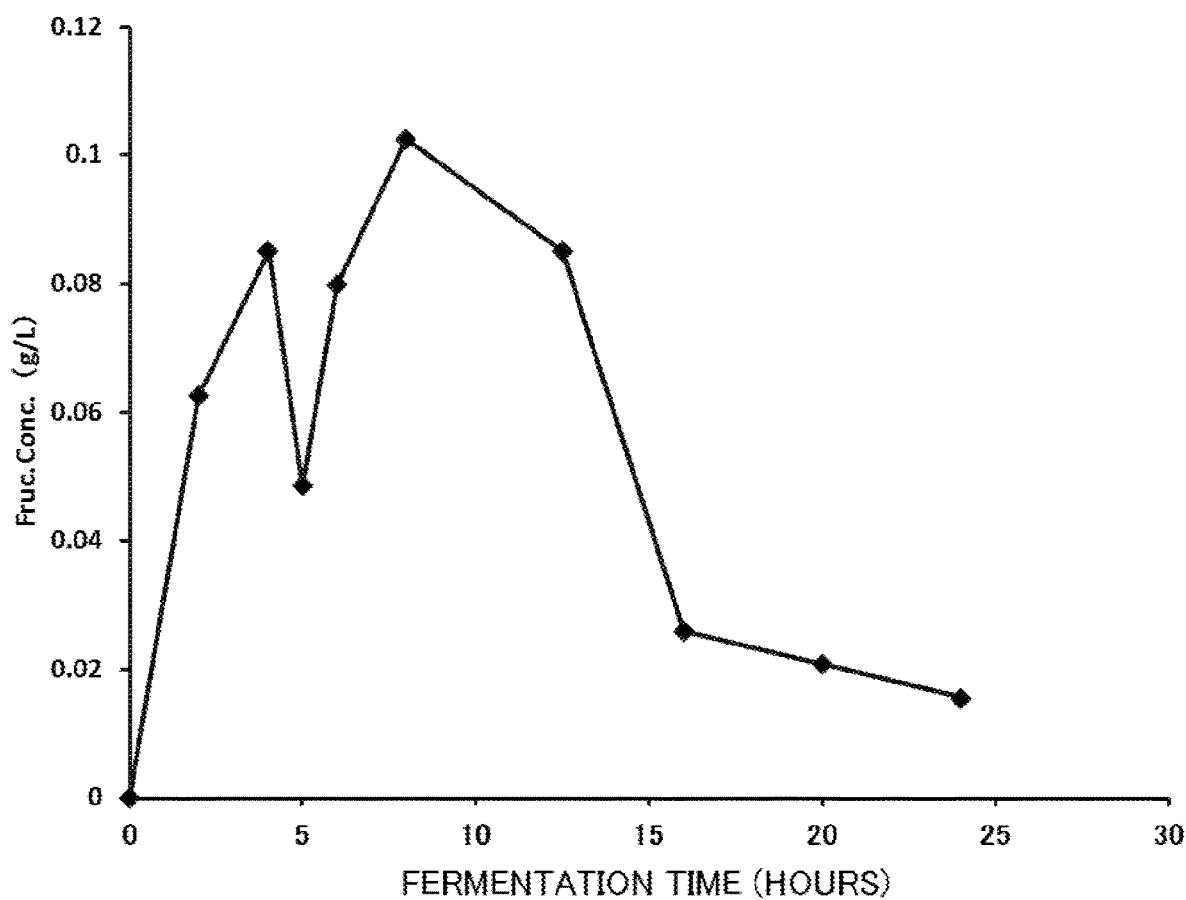
FIG. 11 is a graph depicting a change of fructose concentration with the elapse of time when soy milk is co-fermented at the temperature of 42 degrees Centigrade, with the *Streptococcus thermophilus* K1580 strain that is the bred lactic acid bacteria and the *Lactobacillus debrueckii* subsp. *bulgaricus* K1581 strain that is the bred lactic acid bacteria.

FIG. 11 is a graph depicting a change of fructose concentration with the elapse of time when soy milk is co-fermented with the *Streptococcus thermophilus* K1580 strain and the *Lactobacillus debrueckii* subsp. *bulgaricus* K1581 strain at the temperature of 42° C.

Figure 9:
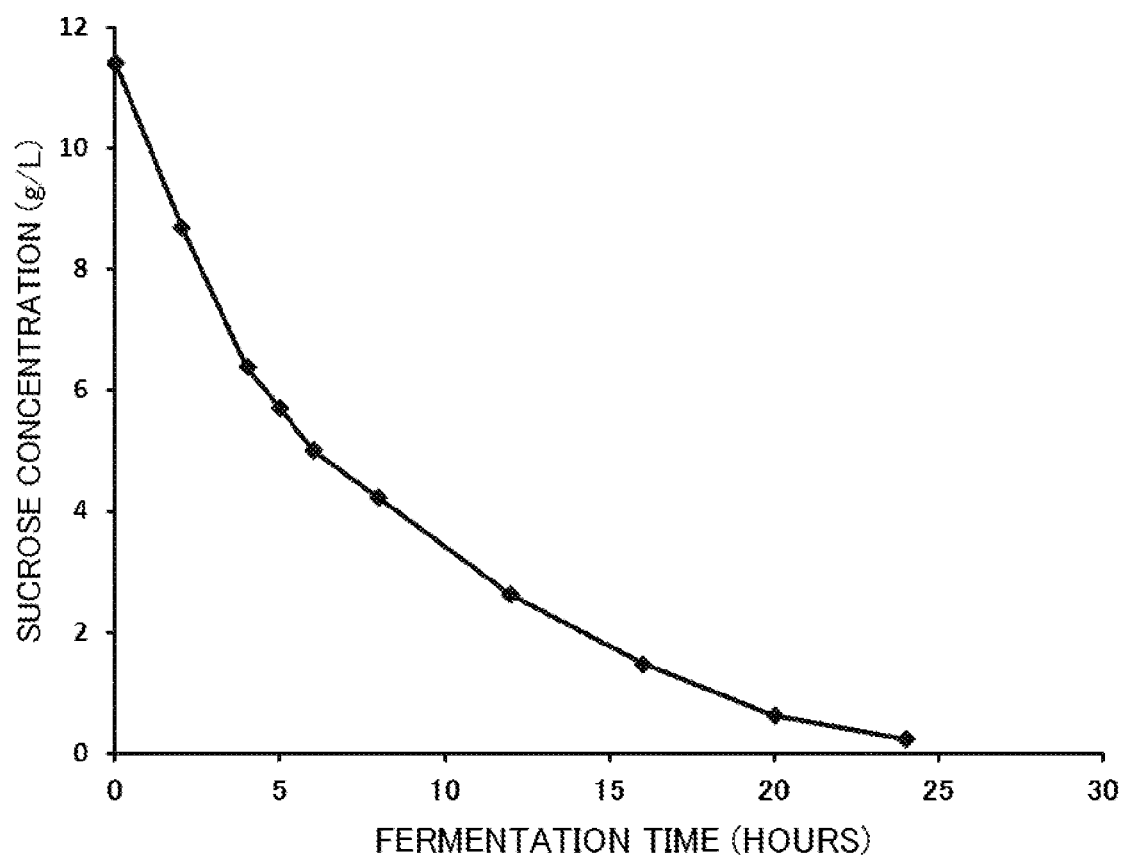
FIG. 9 is a graph depicting a change of sucrose concentration with the elapse of time when soy milk is fermented at the temperature of 42 degrees Centigrade solely by the *Streptococcus thermophilus* K1580 strain that is the bred lactic acid bacteria.
Figure 10:
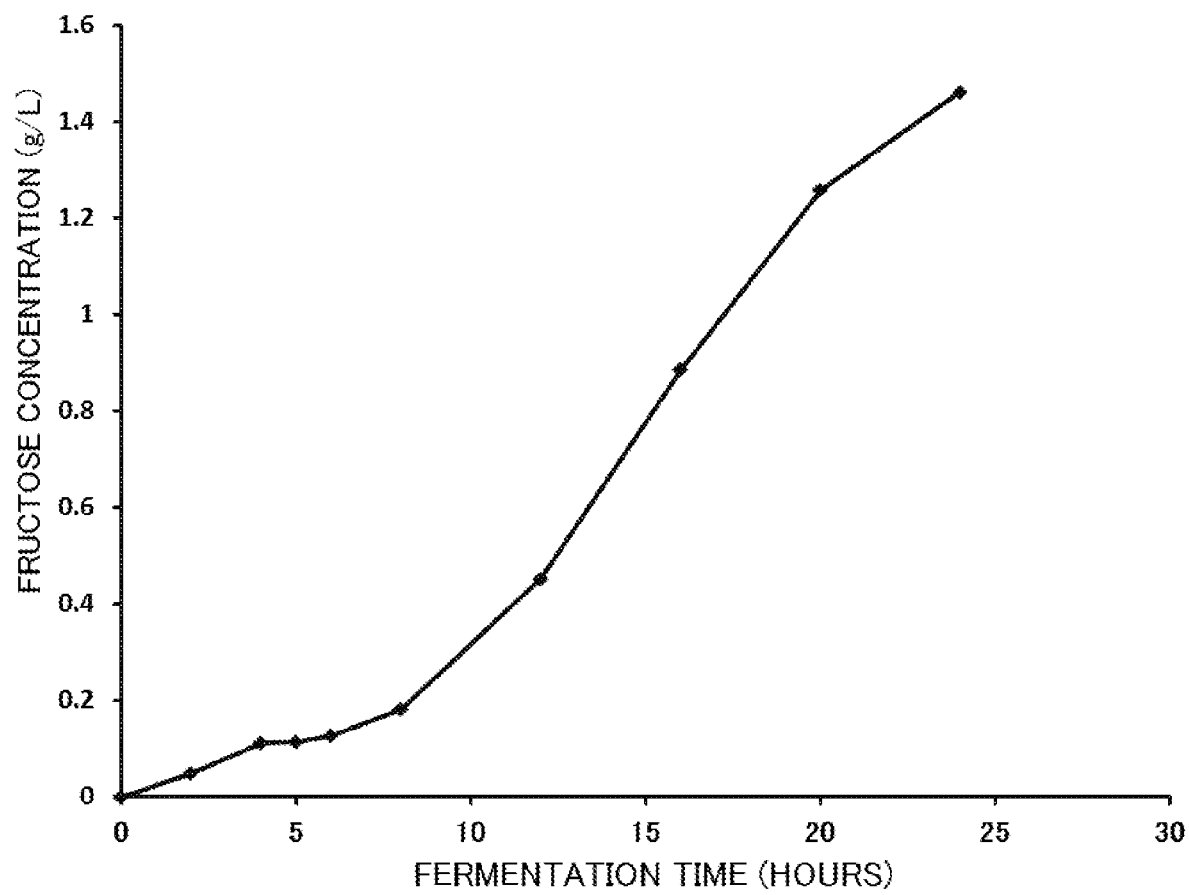
FIG. 10 is a graph depicting a change of fructose concentration with the elapse of time when soy milk is fermented at the temperature of 42 degrees Centigrade solely with the *Streptococcus thermophilus* K1580 strain that is the bred lactic acid bacteria.

On the condition that the *Streptococcus thermophilus* K1580 strain is fermented solely, it was verified that the quantity of sucrose decrease with the elapse of time and then accumulation of fructose arises (FIG. 9 and FIG. 10). On the other hand, when soy milk is co-fermented with the *Streptococcus thermophilus* K1580 strain and the *Lactobacillus debrueckii* subsp. *bulgaricus* K1581 strain, it was verified that a small quantity of fructose is accumulated one time, and subsequently decreases (FIG. 11).

In the light of these two results, it is considered that fructose is metabolized by the K1581 strain, contributing to in generation of D-lactic acid or other aroma component as the result thereof. *Streptococcus thermophilus* is divided into the strains that actively accumulate fructose and the strains that do not accumulate fructose so, and by employing *Streptococcus thermophilus* characterized by such accumulation in fermented product, in soy milk as well, the symbiotic relationship with *Lactobacillus debrueckii* subsp. *bulgaricus* is established, a taste and flavor derived from *Lactobacillus debrueckii* subsp. *bulgaricus* can be imparted, and as a result, it becomes possible to make a soy milk fermented substance with a good taste and flavor.

8. Functional Evaluation Employing Bred Strains

A lactic acid bacteria mixture starter made of the *Streptococcus thermophilus* K1580 strain and the *Lactobacillus debrueckii* subsp. *bulgaricus* K1581 strain that are bred strains was formulated, and by employing this starter, pure soy milk available from Kikkoman Soy Foods Corporation) was fermented at the temperature of 42 degrees Centigrade and for 24 hours, and a soy milk fermented substance was obtained. On the other hand, the *Streptococcus thermophilus* K1580 strain was added to pure soy milk solely, fermentation was carried out at the temperature of 42 degrees Centigrade and for 24 hours, and a soy milk fermented substance was obtained. The respective component analysis values are as follows.

TABLE 1

| S. thermophilus | L. debrueckii | pH | Acidity (%) | D-lactic acid (g/L) | L-lactic acid (g/L) |
|---|---|---|---|---|---|
| K1580 | K1581 | 4.00 | 0.993 | 1.56 | 7.68 |
| K1580 | None | 4.18 | 0.829 | 0 | 7.8 |

Next, D-lactic acid quantity in the fermented substance was formulated by appropriately mixing the soy milk fermented substance and the co-fermented substance. That is, 100% co-fermented substance (sample 1), 40% co-fermented substance (sample 2), 30% co-fermented substance (sample 3), 20% co-fermented substance (sample 4), 15% co-fermented substance (sample 5), 10% co-fermented substance (sample 6), and 100% solely fermented substance (sample 7) were formulated, respectively. The estimated D-lactic acid values and the estimated D/L ratios of the respective samples are as shown in Table 2.

In addition, the respective samples were tasted, and a relationship between D-lactic acid quantity and flavor of soy milk fermented substance was evaluated on the basis of the criteria shown below.

(Criteria)
⊚: Very good taste and flavor
○: Good taste and flavor
Δ: Slightly poor flavor
x: Poor flavor The result is shown in Table 2. As shown in Table 2, it was found that sample 1 to sample 3 each have a good taste and flavor. Therefore, in the soy milk fermented substance, it was found that the flavor is improved by using the *Lactobacillus debrueckii* subsp. *bulgaricus* strain that produces at least 0.4 g/L or more of D-lactic acid. Also, it was clarified that a good taste and flavor is not obtained by merely actively growing only the *Lactobacillus debrueckii* subsp. *bulgaricus*, a balance with growth of *Streptococcus thermophilus* is important, and it is preferable that the D/L lactic acid rate be 0.05 or more.

TABLE 2

|  | Estimated D-lactic acid quantity (g/L) | D/L ratio | Functional evaluation |
|---|---|---|---|
| Sample 1 | 1.56 (actually measured value) | 0.203 | ⊚ |
| Sample 2 | 0.62 | 0.081 | ○ |
| Sample 3 | 0.47 | 0.061 | ○ |
| Sample 4 | 0.31 | 0.04 | Δ |
| Sample 5 | 0.23 | 0.03 | X |
| Sample 6 | 0.15 | 0.019 | X |
| Sample 7 | 0 (actually measured value) | 0 | X |

9. Functional Evaluation of Soy Milk Fermented Substance Obtained By Carrying Out Fermentation Employing Other Commercially Available Mixture Starters The flours of commercially available flour mixture starters for making yogurt (available from Danisco Inc., freeze-dried products including the *Streptococcus thermophilus* strains and the *Lactobacillus bulgaricus* strains YO-MIX300, YO-MIX305, YO-MIX511, YO-MIX863 (wherein all the assigned numbers designate product numbers) were dissolved in sterile water, suspension of the same quantity was inoculated in pure soy milk (available from Kikkoman Soy Foods Corporation), fermentation was carried out at the temperature of 42 degrees Centigrade and for 24 hours, and a soy milk fermented substance was obtained.

On the other hand, the *Streptococcus thermophilus* strains (St. 885 strain, St. 496 strain) derived from the commercially available mixture starters, YO-MIX885, YO-MIX496, were isolated. Also, the *Lactobacillus debrueckii* subsp. *bulgaricus* strains (Lb. 305 strain, Lb. 492 strain, Lb. 601 strain) derived from the commercially available mixture starters YO-MIX305, YO-MIX492, YO-MIX601 were isolated and were respectively stored as glycerol stock bacteria liquors and then the liquors were employed in testing.

In addition, as bred strains, the *Streptococcus thermophilus* K1580 and K1584 strains and the *Lactobacillus debrueckii* subsp. *bulgaricus* K1581 and K1585 strains were employed.

The formulated *Streptococcus thermophilus* strain (St. strain) and the *Lactobacillus debrueckii* subsp. *bulgaricus* strain (Lb. strain) were respectively mixed with each other at the ratio of 1:1 (such as K1580 strain+K1581 strain or St. 885 strain+Lb. 305 strain, for example), fermentation was carried out with 10 mL of pure soy milk (available from Kikkoman Soy Foods Corporation), a pre-fermented substance was obtained. This pre-fermented substance of 1.0% (v/v) was inoculated in pure soy milk (available from Kikkoman Soy Foods Corporation), fermentation was carried out at the temperature of 42 degrees Centigrade and for 24 hours, and a soy milk fermented substance was obtained. The lactic acid analysis values of the respective soy milk fermented substances are shown below.

TABLE 3

| S. thermophilus | L. debrueckii | pH | Acidity (%) | L-lactic acid (g/L) | D-lactic acid (g/L) | D/L ratio |
|---|---|---|---|---|---|---|
| K1580 | K1581 | 4.00 | 0.993 | 7.68 | 1.56 | 0.203 |
| K1584 | K1585 | 4.31 | 0.734 | 6.28 | 0.50 | 0.080 |
| St. 885 | Lb. 305 | 4.27 | 0.752 | 6.46 | 0.75 | 0.116 |
| St. 885 | Lb. 492 | 4.31 | 0.735 | 6.18 | 0.81 | 0.131 |
| St. 885 | Lb. 601 | 4.30 | 0.746 | 6.08 | 0.95 | 0.156 |
| St. 496 | Lb. 305 | 4.56 | 0.556 | 4.72 | 0.68 | 0.144 |
| St. 496 | Lb. 492 | 4.54 | 0.563 | 4.76 | 0.64 | 0.134 |
| St. 496 | Lb. 601 | 4.54 | 0.568 | 4.76 | 0.61 | 0.128 |

| Commercially available starters | pH | Acidity (%) | L-lactic acid (g/L) | D-lactic acid (g/L) | D/L ratio |
|---|---|---|---|---|---|
| YO-MIX300 | 4.37 | 0.617 | 5.42 | 0.00 | 0 |
| YO-MIX305 | 4.35 | 0.639 | 5.64 | 0.00 | 0 |
| YO-MIX511 | 4.26 | 0.691 | 6.28 | 0.00 | 0 |
| YO-MIX863 | 4.25 | 0.692 | 6.34 | 0.04 | 0.006 |

In the respective soy milk fermented substances obtained in the manner as described above, it was added to obtain final concentration of 6.0% (w/v), and functional evaluation was carried out as to flavor or taste. As a result, the fermented soymilk containing no D-lactic acid was not preferred because of its sweetness leading to it. On the other hand, in the fermented soymilk containing 0.4 g/L or more of D-lactic acid, it was found that the acid-sweet balance was obtained and a fermented soymilk with good flavor was obtained. In the light of the foregoing description, in a case where sugar was added to the soy milk fermented substances as well, it was found out that the soy milk fermented substance made by employing the lactic acid bacteria mixture starters according to the present invention (the lactic acid bacteria mixture starters made of the selected or bred strains) have excellent flavors or tastes.

10. Measurement of Physicality of Soy Milk Fermented Substance

The physicality of soy milk fermented substance was measured, and evaluation was carried out. In respect of the evaluation of the physicality, the particle size distribution that is an index indicative of what particle size and what rate of particles are included in the soy milk fermented substance was employed. By measuring the particle size distribution, it is possible to evaluate the feeling on the tongue or smoothness sensed when the fermented product is included in the mouth.

A soy milk fermented substance obtained by fermentation with the commercially available flour mixture starters for making yogurt (available from Danisco Inc., freeze-dried products including the *Streptococcus thermophilus* strains and the *Lactobacillus debrueckii* subsp. *bulgaricus* strains) YO-MIX300, YO-MIX305 (wherein the assigned numbers designate product numbers); and a soy milk fermented substance obtained by fermentation with the selected or bred strains (K1580 strain+K1581 strain, St. 496+Lb. 601, St. 885+Lb. 305) were uniformly stirred and were subjected to a laser diffraction-type particle size distribution measuring instrument (SALD-2200 (Shimadzu Corporation)), and the particle size distribution was measured.

Figure 12:
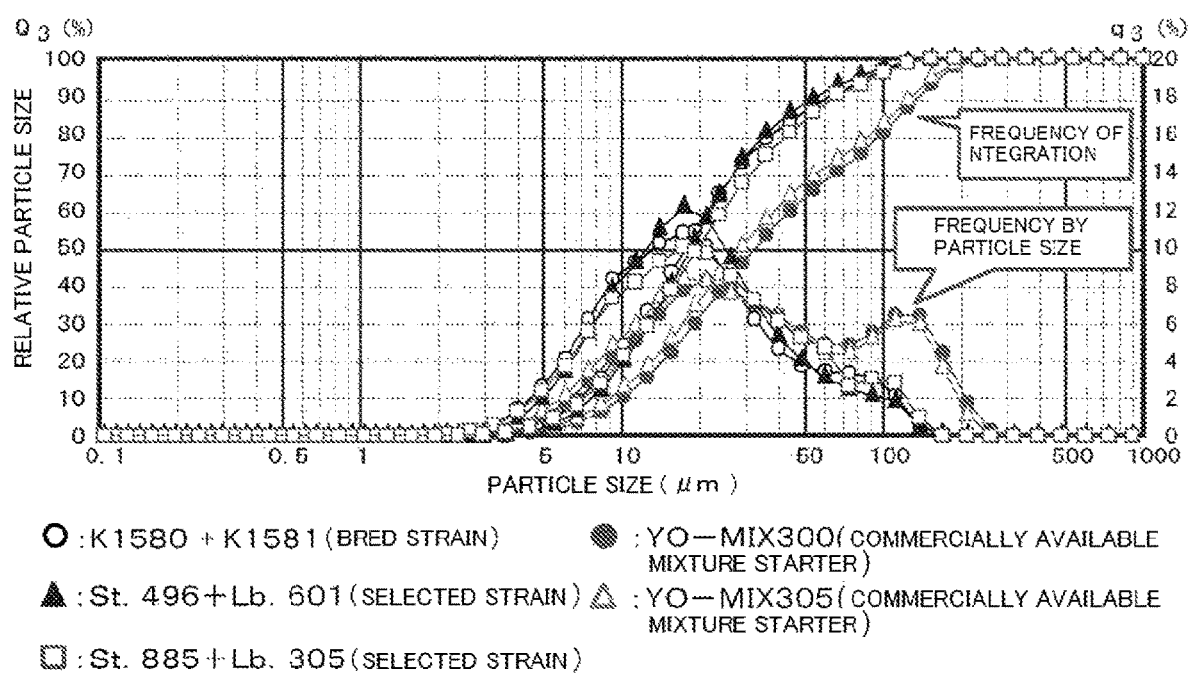
FIG. 12 is a graph depicting a result obtained by measuring a particle size distribution of a soy milk fermented substance obtained by carrying out fermentation by the commercially available mixture starters or the bred strain mixture starters, or alternatively, selected strain mixture starters.

The result of the measurement is shown in FIG. 12. In the graph, the result of integration was also shown together with the appearance frequency of the particle size in the same symbols as to the respective samples. In comparison with the soy milk fermented substances obtained by fermentation with the commercially available starters, in the soy milk fermented substance obtained by fermentation of the selected or bred strains, it was verified that a rate of the particles having the particle size of 100 micrometers or more in all is 10% or less, and the soy milk fermented substance, each of which has a smooth feeling on the tongue, are obtained. This indicates that metabolisms of *Streptococcus thermophilus* and the *Lactobacillus debrueckii* subsp. *bulgaricus* strain at the time of soy milk fermentation were respectively activated by breeding or selection, whereby production of polysaccharides produced by these lactic acid bacteria also became active, and as a result, excessive condensation of soybean protein causing roughness was prevented, and the physicality was improved.

The invention claimed is:

1. A method for producing a fermented soy milk substance, the method comprising:
    (a) selecting a *Streptococcus thermophilus* strain capable of accumulating 0.4 g/L or more of fructose in the fermented substance when inoculated and cultured in a culture medium consisting essentially of unadjusted pure soy milk for a time of 4 to 24 hours at a temperature of 30 to 45° C.;
    (b) selecting a *Lactobacillus delbrueckii* subsp. *bulgaricus* strain capable of accumulating 0.4 g/L or more of D-lactic acid in the fermented substance when inoculated and cultured with the strain selected under step (a) in a culture medium consisting essentially of unadjusted pure soy milk for a time of 4 to 24 hours at a temperature of 30 to 45° C., wherein said *Lactobacillus delbrueckii* subsp. *bulgaricus* strain is not capable of fermenting sucrose;
    (c) inoculating a combination of the strains under (a) and (b) in unadjusted pure soy milk, without adding a sugar source, and
    (d) carrying out fermentation to obtain a fermented soy milk product having a D-lactic acid content of 0.4 g/L or more;
    wherein fermentation is carried out for 4 to 24 hours at a temperature of 30 to 45° C.; and
    wherein the *Streptococcus thermophilus* strain is inoculated at a concentration from $1\times10^5$ to $1\times10^7$ cfu/ml and the *Lactobacillus delbrueckii* subsp. *bulgaricus* strain is inoculated at a concentration of $1\times10^3$ to $1\times10^5$ cfu/ml.

2. The method according to claim 1, wherein the steps (a) and (b) comprise inoculating and culturing in unadjusted pure soy milk, respectively.

3. The method according to claim 2, wherein the steps (a) and (b) comprise, respectively, inoculating and culturing simultaneously.

4. The method according to claim 1, wherein the steps (a) and (b) comprise, respectively, inoculating and culturing simultaneously.

5. The method according to claim 1, further comprising making the rate of the fermented soy milk substance having a particle size of 100 micrometers or more, 10% or less in all particle size distribution.

6. The method according to claim 2, further comprising making the rate of the fermented soy milk substance having a particle size of 100 micrometers or more, 10% or less in all particle size distribution.

7. The method according to claim 3, further comprising making the rate of the fermented soy milk substance having a particle size of 100 micrometers or more, 10% or less in all particle size distribution.

8. The method according to claim 1, wherein the *Lactobacillus delbrueckii* subsp. *bulgaricus* strain is capable of accumulating 0.4 g/L to 1.6 g/L of D-lactic acid in the fermented substance.

9. The method according to claim 1, wherein fermentation is carried out for 24 hours at a temperature of 42° C.

10. A method for producing a fermented soy milk substance, the method comprising:
    (a) selecting a *Streptococcus thermophilus* strain capable of accumulating 0.4 g/L or more of fructose in the fermented substance when inoculated and cultured in a culture medium consisting essentially of soy milk not produced from a powdered soy milk for a time of 4 to 24 hours at a temperature of 30 to 45° C.;
    (b) selecting a *Lactobacillus delbrueckii* subsp. *bulgaricus* strain capable of accumulating 0.4 g/L or more of D-lactic acid in the fermented substance when inoculated and cultured with the strain selected under step (a) in a culture medium consisting essentially of soy milk not produced from a powdered soy milk for a time of 4 to 24 hours at a temperature of 30 to 45° C., wherein said *Lactobacillus delbrueckii* subsp. *bulgaricus* strain is not capable of fermenting sucrose;
    (c) inoculating a combination of the strains under (a) and (b) in soy milk not produced from a powdered soy milk without adding a sugar source, and
    (d) carrying out fermentation to obtain a fermented soy milk product having a D-lactic acid content of 0.4 g/L or more;
    wherein fermentation is carried out for 4 to 24 hours at a temperature of 30 to 45° C.; and
    wherein the *Streptococcus thermophilus* strain is inoculated at a concentration from $1\times10^5$ to $1\times10^7$ cfu/ml and the *Lactobacillus delbrueckii* subsp. *bulgaricus* strain is inoculated at a concentration of $1\times10^3$ to $1\times10^5$ cfu/ml.

* * * * *